United States Patent [19]
Gerardo

[11] Patent Number: 5,292,345
[45] Date of Patent: Mar. 8, 1994

[54] PORTABLE PHOTONEURONIC ENERGIZER

[76] Inventor: Ernesto A. Gerardo, 4507 Groveland Rd., University Heights, Ohio 44118

[21] Appl. No.: 427,984

[22] Filed: Oct. 30, 1989

Related U.S. Application Data

[63] Continuation of Ser. No. 88,383, Aug. 24, 1987, abandoned.

[51] Int. Cl.⁵ .............................................. A61N 5/00
[52] U.S. Cl. ......................................... 607/88; 607/91
[58] Field of Search ......................... 128/395–398, 128/24.1, 380, 23, 76.5; 351/203; 362/106

[56] References Cited

U.S. PATENT DOCUMENTS

| | | | |
|---|---|---|---|
| 669,949 | 3/1901 | Underwood | 128/380 X |
| 765,530 | 7/1904 | Webb | 128/380 |
| 3,621,838 | 11/1971 | Harding et al. | 128/82.1 |
| 3,670,193 | 6/1972 | Thorington et al. | 313/487 |
| 3,953,725 | 4/1976 | Ketler et al. | 362/106 X |
| 4,044,756 | 8/1977 | Hamilton et al. | 128/2 N |
| 4,057,054 | 11/1977 | Giannone | 357/203 |
| 4,399,492 | 8/1983 | Kolesar | 362/106 |
| 4,553,534 | 11/1985 | Stiegler | 128/24.1 |
| 4,593,683 | 6/1986 | Blaha | 362/106 X |

FOREIGN PATENT DOCUMENTS 2371935  7/1978  France ............................ 128/395

OTHER PUBLICATIONS

"Seasonal Affective Disorder" Rosenthal et al, Gen. Psychiatry, vol. 41 Jan. 1984.
"Let the sun shine", Phillips, Dec. 11, 1985 The Washington Post.

*Primary Examiner*—Mark S. Graham
*Attorney, Agent, or Firm*—John S. Benefiel

[57] ABSTRACT

A portable photoneuronic energizer for providing a portable full spectrum light source to treat Seasonal Affective Disorder comprising head support means, a full spectrum light mounted on the head support means and positioned for indirect light to enter the user's eyes.

5 Claims, 1 Drawing Sheet

PORTABLE PHOTONEURONIC ENERGIZER

This is a continuation of co-pending application Ser. No. 07/088,383 filed on Aug. 24, 1987, abandoned.

BACKGROUND OF THE INVENTION

Recent medical advances (*American Journal of Psychiatry*, Rosenthal et al, 142:2, 163–70) have demonstrated that light can be used to treat certain types of depression, specifically, Seasonal Affective Disorder (SAD). SAD is a condition in which an individual feels depressed and lethargic with a tendency to overeat, oversleep and crave carbohydrates. In its more severe forms, the affected person is totally withdrawn and unable to successfully function in society. This disorder is most commonly observed during the winter months, when skies are cloudy and overcast, with long periods of little or no natural sunlight exposure. Many persons experiencing "winter blues", or "cabin fever" are probably experiencing some lesser degree of SAD or light hunger. Most persons affected note marked relief from their symptoms of depression after exposure to sunlight, for instance during and following winter vacations to sunny climates.

Current scientific research in the physiology behind this phenomenon points to the effect of light on the retinohypothalamic tract in either suppressing or stimulating production of certain neurotransmitters, i.e. melatonin and serotonin respectively, known to be responsible for neuroendocrine changes of circadian rhythm in animal models and of mood and affect in human models. While current light therapy utilizing stationary indoor apparatus is being applied to patients with bipolar type II SAD in psychiatric clinical settings, it is felt by the inventor that the normal individual experiencing the common "winter blues" would receive benefit from a portable light source administering experimentally determined minimal doses of light to suppress melatonin, thus producing an anti-depressant effect. Detailed information on the neurophysiology of daily exposure to light on both animal and human models is presented in *Science*, Lewy et al, 1980; 210:1267.

There are devices in the prior art providing light exposure for the treatment of SAD, but these devices are large, bulky, stationary metal enclosures having banks of fluorescent daylight tubes commonly referred to as "light boxes". The proposed invention is a full spectrum portable light source of 5000° K. sufficient power to deliver a premeasured dose of light of at least 500 lux over a period of time from a position indirect to the user's eyes. In effect with this invention, the user is exposed only to the type and amount of light he would experience if he were in a bright, sunny environment.

The present invention is an improvement over existing fixed devices in that it provides a portable light source worn on the user's head, not only for therapeutic outpatient use by those individuals suffering from SAD, but for a person living in those latitudes and geographic locations that experience prolonged, low-sunlight winter conditions. It is anticipated that some percentage of the population experiences SAD in such mild to moderate severity that their condition goes undiagnosed because it did not warrant psychiatric consultation. It is this group that will benefit from the proposed invention in the form of elevated mood, better overall performance, less susceptibility to stress and consequent depression, and higher energized levels for all activities of daily living. Insofar as this effect will be achieved by natural physiologic process using full spectrum light as neuroendoctrine stimulant, it is emphasized that the user would experience no ill effect than he normally would upon being exposed to natural sunlight of the same duration and intensity.

SUMMARY OF THE INVENTION

In accordance with the present invention there is provided an improved portable head attachment device for therapeutic treatment of Seasonal Affective Disorder commonly called "winter blues" or "cabin fever" comprising a head support means, full spectrum light source means affixed to said head support means (a portable photoneuronic energizer) comprising head support means for mounting on the head of a user person suffering Seasonal Affective Disorder, full spectrum light source means affixed to said head mounted support means and being positioned for incident light to enter the eyes of the user person, power source means for illuminating said light source means, and conducting means for conducting power from said power source means to said light source means.

Accordingly, it is an object of the invention to provide a portable light source to treat Seasonal Affective Disorder.

Another object of the invention is to provide a portable photoneuronic energizer that is simple, effective and inexpensive to manufacture.

It is a further object to provide a portable photoneuronic energizer to treat Seasonal Affective Disorder that is effective, easy to use and will not interrupt the user from performing other normal daily functions.

Other objects and advantages of the invention will appear from the following detailed description of preferred embodiments of the invention, reference being made to the accompanying drawings.

DETAILED DESCRIPTION OF THE INVENTION

Figure 1:
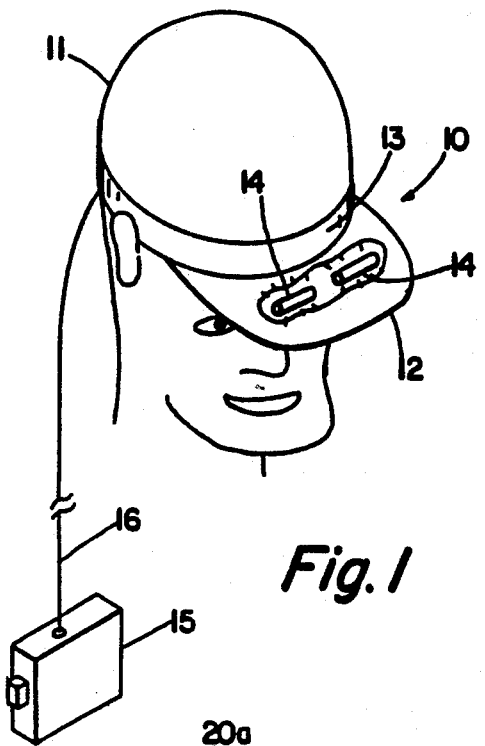
FIG. 1 is a perspective view of one embodiment of a cap mounted light source according to the present invention.

Referring to FIG. 1 there is illustrated one embodiment of the portable photoneuronic energizer of the invention shown generally at 10. A fabric or polystyrene cap 11 having a visor 12 is shown being worn by a user person. The cap 11 has a flexible band 13 made of plastic material of sufficient strength to support the visor 12 which holds lamp 14. A typical material for the band 13 would be polystyrene.

One or more lamps 14 are affixed to the visor 12 as shown in FIG. 1 made of a material such as polystyrene that is rigid and of sufficient strength to support the lamp(s) as shown in FIG. 1 one may be sufficient, or more may be used depending on manufacturing specifications. The light source 12 must be capable of providing light intensity of at least 500 lux. Further, the light required must be full spectrum approximating natural outdoor daylight at a range of 5000° K. to 7000° K. color temperature. Full spectrum fluorescent bulbs or tubes as described in U.S. Pat. No. 3,670,193 are required wherein light is emitted in the wavelength of 400 nanometers (red) to 740 nanometers (violet) at said temperature range 5000° K. to 7500° K.

Fluorescent light bulbs that simulate the full color spectrum and generate the approximate ultraviolet microwatts, per lumen of natural sunlight are required by the present invention for the successful treatment of persons suffering from Seasonal Affective Disorder.

Figure 2:
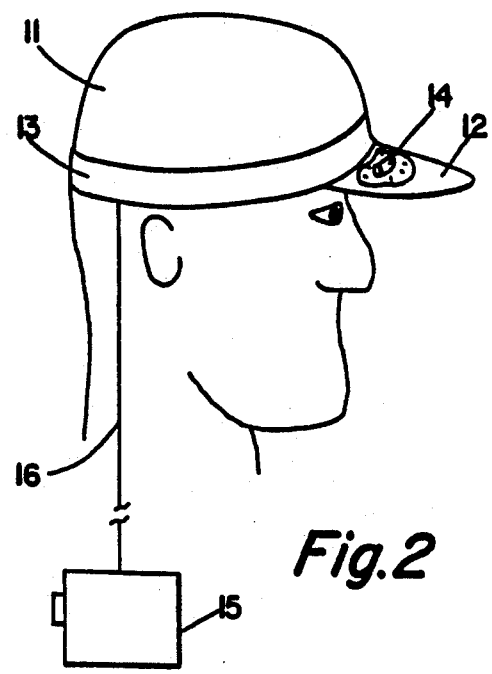
FIG. 2 is a side view of FIG. 1

The position of said light source means is such that indirect light emitted will enter the eyes of the user suffering from Seasonal Affective Disorder. That is, light incident or indirect to the retina will enter in a manner similar to natural outdoor light emitted by the sun. It is the absence of this incident sunlight in Northern environments that leads to Seasonal Affective Disorder or "cabin fever". The position of lamps 14 on visor 12 as shown in FIG. 1 and FIG. 2 produce said incident light similar to outdoor sunlight.

Power for illuminating lamps 12 is transmitted from D.C. electric battery source 15 by means of two insulated electrical wires 16. An electric battery of sufficient voltage Direct Current that would deliver ample power for providing 15-40 watts to illuminate the lamps 14 above to provide 535 to 2340 lux at 5000° K. to 7500° K. which approximate natural sunlight.

Figure 3:
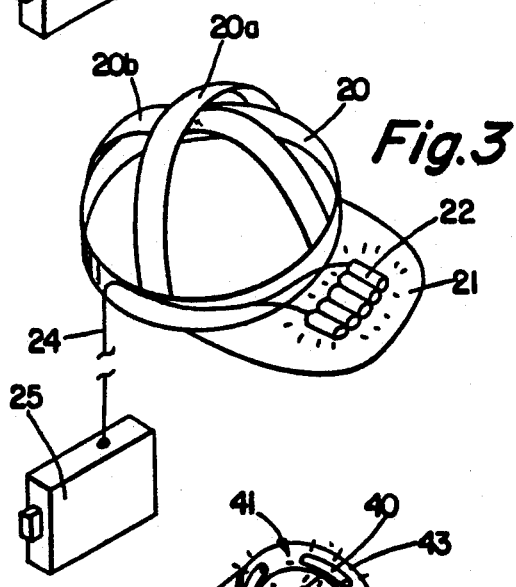
FIG. 3 is a perspective view of a second embodiment showing a head clamp with a visor of the invention.

In FIG. 3 there is shown a second embodiment of the invention having a head band clamp 20 with a visor 21 typically made of polystyrene as stated above. Also connected to head band clamp 20 are dome strips 20a and 20b to prevent slipping down over the user's head. Visor 21 has fluorescent bulbs (tubes) mounted at 22 to provide incident light as stated above. Power from D.C. battery (12-30 volts) is transmitted to lamp 22 through electrical wires 24.

Figure 4:
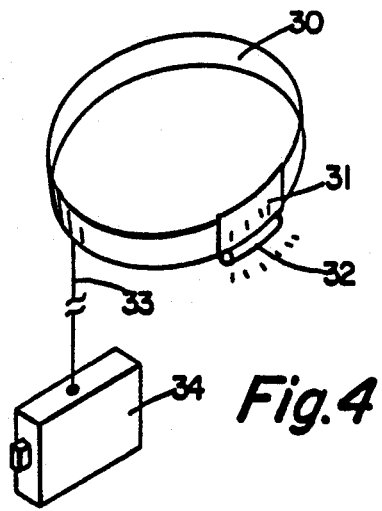
FIG. 4 is a perspective view of a third embodiment showing a head clamp mounted light source.

FIG. 4 shows a third embodiment of the invention showing a further head support means having a head band 30, a mounting plate 31 affixed to said head band 30, a full spectrum lamp 32, electrical wires 33 and electrical storage battery 34.

Figure 5:
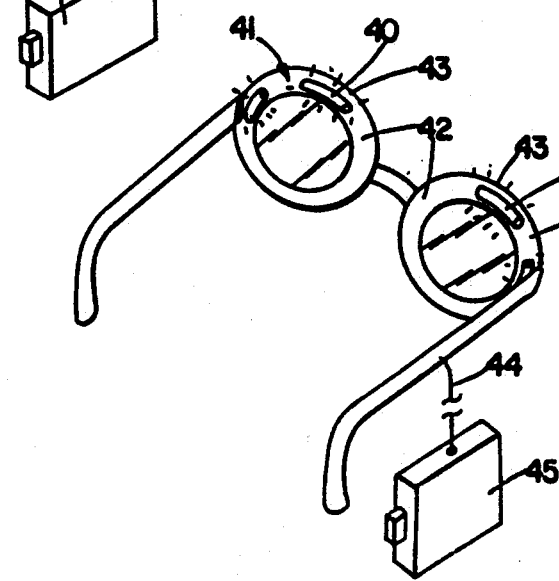
FIG. 5 is a perspective view of a fourth embodiment showing a light source mounted on eyeglass frames.

In FIG. 5 there is shown a fourth embodiment of the invention wherein said light source means are fluorescent bulbs (tubes) 40 affixed to eyeglass frame 41 on the eye rims 42 at the top 43. Again the lamps 40 are illuminated by power from an electric storage battery 45 of 12V to 40V D.C. through electric conducting wires 44. The storage battery could be placed in a pocket of clothing worn by the user person or clipped to a belt.

While specific embodiments of the invention have been described and illustrated, it is to be understood that these embodiments are provided by way of example only and that the invention is not to be construed as being limited thereto, but only by the proper scope of the following claims:

What is claimed is:

1. A portable photoneuronic energizer, comprising head support means for mounting on the head of a user person suffering Seasonal Affective Disorder, at least one full spectrum fluorescent light bulb affixed to said head support means and being positioned above and forward of the user person's eyes wherein indirect light from said fluorescent light bulb when illuminated enters the eyes of the user person, said fluorescent light bulb being limited to one that emits light in the wave length of 400 nanometers (red) to 740 nanometers (violet) at a temperature range of 5000° K. to 7000° K., electric power means for illuminating said fluorescent light bulb of at least 500 lux, and electric circuit means for conducting electric power from said electric power means to said fluorescent light bulb to illuminate said fluorescent light bulb in continuous, uninterrupted light emission.

2. A photoneuronic energizer as defined in claim 1 wherein said electric circuit means for conducting power from said electric power means to said fluorescent bulb are electric wires and said electric power means is an electric storage battery.

3. A photoneuronic energizer as defined in claim 1 wherein said head support means is a cap.

4. A photoneuronic energizer as defined in claim 1 wherein said head mounted support means is a head clamp having a mounting plate and said fluorescent light bulb is affixed to said mounting plate in a position wherein indirect light enters the eyes of the user person.

5. A device for shining light into an eye of a patient for the treatment of light responsive psychological and/or psychiatric conditions comprising:

a head visor means for mounting on the head of a patient, said visor means when worn comprises a support means having an upper and lower side, said support means being fixed above and forward of the patient's eyes and having light projecting and light generating means supported by said support means at said lower side thereof, for generating a steady beam of light sufficient to reach the eye at an intensity of at least 1,000 lux and for directing said steady beam of light into the eye of the patient in a manner so as to avoid interfering with the patient's principle field of vision.

* * * * *